US007029846B2

(12) United States Patent  
Rana et al.

(10) Patent No.: US 7,029,846 B2
(45) Date of Patent: Apr. 18, 2006

(54) SITE-SPECIFIC PROTEIN MODIFICATION

(75) Inventors: Tariq M. Rana, Shrewsbury, MA (US); Natarajan Tamilarasu, Highland Park, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 486 days.

(21) Appl. No.: 09/972,016

(22) Filed: Oct. 4, 2001

(65) Prior Publication Data

US 2002/0106767 A1 Aug. 8, 2002

Related U.S. Application Data

(60) Provisional application No. 06/237,881, filed on Oct. 4, 2000.

(51) Int. Cl.
*C12Q 1/68* (2006.01)
(52) U.S. Cl. .............................. 435/6; 514/2; 436/172; 530/345
(58) Field of Classification Search .................... 435/6; 514/2; 436/172; 530/345
See application file for complete search history.

(56) References Cited

U.S. PATENT DOCUMENTS

| | | | | |
|---|---|---|---|---|
| 3,714,140 A * | 1/1973 | Sipos | ......................... | 530/334 |
| 3,715,434 A * | 2/1973 | Mende | ......................... | 514/5 |
| 3,875,207 A * | 4/1975 | Iselin et al. | .................. | 530/337 |
| 3,944,538 A * | 3/1976 | Bodanszky | .................. | 530/339 |
| 4,568,640 A * | 2/1986 | Rubin | ........................ | 435/69.4 |
| 5,945,283 A * | 8/1999 | Kwok et al. | .................... | 435/6 |
| 5,958,700 A * | 9/1999 | Nadeau et al. | .................. | 435/6 |
| 6,180,347 B1 * | 1/2001 | Iida et al. | ....................... | 435/6 |
| 6,316,194 B1 * | 11/2001 | Karn et al. | ..................... | 435/6 |
| 6,503,713 B1 * | 1/2003 | Rana | .............................. | 435/6 |
| 6,573,045 B1 * | 6/2003 | Karn et al. | ..................... | 435/6 |

OTHER PUBLICATIONS

Odom O. W., Biochemistry 23, 5069, 1984.*
Odom O. W., Biochemistry 19, 5947, 1980.*
Odom O. W. Biochemistry 19, 1980.*
Odom O. W. Biochemistry 23, 1984.*
Matsumoto, C., Bioorganic & Medicinal Chemistry Letters (2000), 10(16), 1857-1861.*
Tamilarasu, Natarajan, Bioconjugate Chemistry, (Mar.-Apr., 2001) vol. 12, No. 2, pp. 135-138.*
Kumagai, Bioorg Med Chem Letters 10, 377 (2000).*
Murchie, Alastair, Journal of Molecular Biology, (Feb. 20, 2004) vol. 336, No. 3, pp. 625-638.*
Zhang, J. Biol. Chem. 275, 34314, (2000).*
Czworkowski J, Biochemistry, (May 14, 1991) 30 (19) 4821-30.*

Klostermeier D, Biochemistry, (Oct. 24, 2000) 39 (42) 12970-8.*
Odom O W, Biochemistry, (Dec. 4, 1990) 29 (48) 10734-44.*
Berkhout et al., "Tat trans-activates the Human Immunodeficiency Virus Through a Nascent RNA Target," Cell, vol. 59, (Oct. 20, 1989) pp. 273-282.
Calnan et al., "Analysis of arginine-rich peptides from the HIV Tat protein reveals unusual featuures of RNA—protein recognition," Genes Dev., 5, (1991) pp. 201-210.
Calnan et al., "Arginine-Mediated RNA Recognition: The Arginine Fork," Science, vol. 252, (May 24, 1991) pp. 1167-1171.
Churcher et al., "High Affinity Binding of TAR RNA by the Human Immunodeficiency Virus Type-1 *tat* Protein Requires Base-pairs in the RNA Stem and Amino Acid Residues Flanking the Base Region," J. Mol. Biol., vol. 230, No. 1, (Mar. 5, 1993) pp. 90-110.
Clegg, "Fluorescence resonance energy transfer and nucleic acids," Methods Enzymol., vol. 211, (1992) pp. 353-388.
Cornish et al., "Site-Specific Protein Modification Using a Ketone Handle," J. Am. Chem. Soc., vol. 118, (1996) pp. 8150-8151.
Cordingley et al., "Sequence-specific interaction of Tat protein and Tat peptides with the transactivation-responsive sequence element of human immunodeficiency virus type 1 *in vitro*," Proc. Natl. Acad. Sci., vol. 87, No. 22, (Nov. 1990) pp. 8985-8989.
Cullen, "HIV-1 auxiliary proteins: making connections in a dying cell," Cell, vol. 93, No. 5, (May 29, 1998) pp. 685-692.
Dingwall et al., "Human immunodeficiency virus 1 tat protein binds trans-activation-responsive region (TAR) RNA *in vitro*," Proc. Natl. Acad. Sci., vol. 86, No. 18, (Sep. 1989) pp. 6925-6929.
Dingwall et al., "HIV-1 *tat* protein stimulations transcription by binding to a U-rich bulge in the stem of the TAR RNA Structure," EMBO J., vol. 9, No. 12, (1990) pp. 4145-4153.
Dong et al., "Synthesis and biological activities of fluorescent acridine-containing HIV-1 nucleocapsid proteins for investigation of nucleic acid-NCp7 interactions," J. Peptide Res., vol. 50, No. 1, (Jul. 1997), pp. 269-278.

(Continued)

*Primary Examiner*—Bruce R. Campell
*Assistant Examiner*—David Lukton
(74) *Attorney, Agent, or Firm*—Hoffmann & Baron, LLP (57) ABSTRACT

Site-specific modified proteins and method for producing site-specific modified proteins using amino acid analogs are disclosed. Methods for labeling proteins at a desired site in the presence of nucleophilic side chains, including lysine and cysteine side chains, are also disclosed. Methods for labeling the site-specific modified proteins are also disclosed.

11 Claims, 8 Drawing Sheets

OTHER PUBLICATIONS

Falchetto et al., "The Plasma Membrane $Ca^{2+}$ Pump Contains a Site That Interacts with Its Calmodulin-binding Domain," J. Biol. Chem., vol. 266, No. 5, (Feb. 15, 1991) pp. 2930-2936.

Geoghegan et al., "Site-Directed Conjugation of Nonpeptide Groups to Peptides and Proteins via Periodate Oxidation of a 2-Amino Alcohol. Application to Modification at N-Terminal Serine," Bioconjugate Chem. vol. 3, No. 2, (Mar. 4, 1992) pp. 138-146.

Huq et al., "Probing the proximity of the core domain of an HIV-1 Tat fragment in a Tat—TAR complex by affinity cleaving," Biochemistry, vol. 36, (1997) pp. 12592-12599.

Jakobovits et al. "A discrete Element 3' of Human Immunodeficiency Virus 1 (HIV-1) and HIV-2 mRNA Initiation Sites Mediates Transcriptional Activation by an HIV *trans* Activator," Mol. Cell. Biol., vol. 8, No. 6, (May 1988) pp. 2555-2561.

Jones et al., "Control of RNA Initiation and Elongation at the HIV-1 Promoter," Annu. Rev. Biochem., vol. 63, (1994) pp. 717-743.

Jones, "Taking a new TAK on Tat transactivation," Genes & Dev., vol. 11, No. 20, (Oct. 15, 1997), pp. 2593-2599.

King et al., "A cleavage method which minimizes side reactions following Fmoc solid phase peptide synthesis," Int J. Peptide Protein Res., vol. 36, No. 3, (Sep. 1990) pp. 255-266.

Lohse et al., "Fluorescein-Conjugated Lysine Monomers for Solid Phase Synthesis of Fluorescent Peptides and PNA Oligomers," Bioconjugate Chem., vol. 8, No. 4, (Jul. 8, 1997) pp. 503-509.

Long et al., "Interaction of human immunodeficiency virus type 1 Tat-derived peptides with TAR RNA," Biochemistry, vol. 34, No. 27, (Jul. 11, 1995) pp. 8885-8895.

Means et al., "Chemical modification of proteins: history and application," Bioconjugate Chem., vol. 1, No. 1, (Jan. 2, 1990) pp. 2-12.

Muesing et al., "Regulation of mRNA Accumulation by a Human Immunodeficiency Virus *Trans*-Activator Protein," Cell, vol. 48, No. 4, (Feb. 27, 1987) pp. 691-701.

Muller et al., "Interaction of fluorescently labeled dideoxynucleotides with HIV-1 reverse transcriptase," Biochemistry, vol. 30, No. 15, (Apr. 16, 1991) pp. 3709-3715.

Ping et al., "Dynamics of RNA—protein interactions in the HIV-1 Rev-RRE complex visualized by 6-thioguanosine-mediated photocrosslinking," RNA, vol. 3, No. 8, (Aug. 1997) pp. 850-860.

Ploug et al., "Photoaffinity Labeling of the Human Receptor for Urokinase-Type Plasminogen Activator Using a Decapeptide Antagonist. Evidence for a Composite Ligand-Binding Site and a Short Interdomain Separation," Biochemistry, vol. 37, (1998) pp. 3612-3622.

Ranganathan et al., "Protein Engineering: Design of Single-Residue Anchored Metal-Uptake Systems," Inorg. Chem., vol. 38, No. 5, (Mar. 8, 1999) pp. 1019-1023.

Rosen et al., "The Location of *Cis*-Acting Regulatory Sequences in the Human T Cell Lymphotropic Virus Type III (HTLV-III/LAV) Long Terminal Repeat," Cell, vol. 41, No. 3, (Jul. 1985) pp. 813-823.

Shah et al., "Synthesis of uridine phosphoramidite analogs: Reagents for site-specific incorporation of photoreactive sites into RNA sequences," Bioconjugate Chem., vol. 5, (1994), pp. 508-512.

Tinoco et al., "RNA folding," Nucl. Acids & Mol., Biol. vol. 4, (1990) pp. 205-226.

Wang et al., "RNA conformation in the Tat—TAR complex determined by site-specific photo-cross-linking," Biochemistry, vol. 35, No. 28, (May 21, 1996) pp. 6491-6499.

Weeks et al., "RNA Recognition by Tat-Derived Peptides: Interaction in the Major Groove?," Cell, vol. 66, No. 3, (Aug. 9, 1991) pp. 577-588.

Yang et al., "Fluorescence resonance energy transfer as a probe of DNA structure and function," Methods Enzymol. vol. 278, No. 20, (1997) pp. 417-444.

* cited by examiner

Scheme I a. $CH_3COCl$-$AlCl_3$/Nitrobenzene, 100 °C, 6 h; b. Fmoc-OSu-$Na_2CO_3$/Dioxane-$H_2O$

SEQUENCE LISTING

```
<160> NUMBER OF SEQ ID NOS: 3

<210> SEQ ID NO 1
<211> LENGTH: 29
<212> TYPE: RNA
<213> ORGANISM: Human immunodeficiency virus
<220> FEATURE:
<221> NAME/KEY: misc_feature
<223> OTHER INFORMATION: TAR RNA of HIV (bp 17-45)
<221> NAME/KEY: misc_feature
<223> OTHER INFORMATION: Acceptor dye molecule, Rhodamine, bound to bp 45

<400> SEQUENCE: 1
gccagaucug agccugggag cucucuggc                                          29

<210> SEQ ID NO 2
<211> LENGTH: 10
<212> TYPE: PRT
<213> ORGANISM: Human immunodeficiency virus

<400> SEQUENCE: 2

Tyr Gly Arg Lys Lys Arg Arg Gln Arg Arg
1               5                   10

<210> SEQ ID NO 3
<211> LENGTH: 10
<212> TYPE: PRT
<213> ORGANISM: Human immunodeficiency virus
<220> FEATURE:
<221> NAME/KEY: MISC_FEATURE
<222> LOCATION: (1)..(1)
<223> OTHER INFORMATION: Xaa is Acetyl-Tyr which replaced Tyr-47 in the
      Tat derived peptide (amino acids 47-56)

<400> SEQUENCE: 3

Xaa Gly Arg Lys Lys Arg Arg Gln Arg Arg
1               5                   10
```

SITE-SPECIFIC PROTEIN MODIFICATION

CROSS-REFERENCE TO RELATED APPLICATIONS

The present application claims priority to U.S. Provisional Application No. 60/237,888, filed Oct. 4, 2000, the entire disclosure of which is incorporated herein by reference.

GOVERNMENT INTEREST

This work was supported by National Institutes of Health Grant AI 41404. This invention was made with government support. The government may own certain rights in the present invention.

INTRODUCTION

Site-specific modification of proteins and peptides with reporter molecules provides a powerful research tool in chemistry and biology. However, selective chemical modification of proteins involves covalent derivatization of the functional group (e.g., —$NH_2$ and —SH) of a single, unique amino acid residue in the protein without causing any effect on other functional groups. (Means, G. E., and Feeney, R. E. (1990) *Chemical modification of proteins: history and application, Bioconjugate Chem.* 1, 2–12).

It is difficult to produce site-specific modified proteins in proteins containing lysine and cysteine residues. Since the reaction of ketone and aldehyde with a hydrazide is orthogonal to the functional groups present in proteins, this chemistry has been used to label peptides and proteins by the oxidation of N-terminal serine to the corresponding aldehyde and subsequent coupling with an appropriate hydrazide. (Geoghegan, K. F., and Stroh, J. G. (1992) *Site-Directed Conjugation of Nonpeptide Groups to Peptides and Proteins via Periodate Oxidation of a 2-Amino Alcohol, Application to Modification at N-Terminal Serine, Bioconjugate Chem.* 3, 138–146). Schultz and co-workers have introduced a ketone handle into a unique site in a protein by unnatural amino acid mutagenesis which was subsequently modified with a fluorescein derivative. (Cornish, V. W., Hahn, K. M., and Schultz, P. G. (1996) *Site-Specific Protein Modification Using a Ketone Handle, J. Am. Chem. Soc.* 118, 8150–8151). As a result, the attachment of a reporter molecule at a specific site in proteins containing multiple lysine and cysteine residues is difficult to achieve and in most cases requires some orthogonal protection of these side chains.

Amino acid analogues pre-conjugated with structural probes have also been used in the solid phase peptide synthesis to produce site-specific modified proteins. (Falchetto, R., Vorherr, T., Brunner, J., and Carafoli, E. (1991) *The Plasma Membrane Ca 2+ Pump Contains a Site That Interacts with Its Calmodulin-binding Domain, J. Biol. Chem.* 266, 2930–2936, Lohse, J., Neilson, P. E., Ilarrit, N., and Dahl, O. (1997) *Fluorescein-Conjugated Lysine Monomers for Solid Phase Synthesis of Fluorescent Peptides and PNA Oligomers, Bioconjugate Chem.* 8, 503–509; Dong, C. Z., De Roequigny, H., Remy, E., Mellac, S., Fournic-Zaluski, M. C., and P., R. B. (1997) *Synthesis and biological activities of fluorescent acridine-containing HIV-1 proteins for investigation of nucleic acid-$NC_p7$ interactions, J. Peptide Res.* 50, 269–278; Ploug, M., Ostergaard, S., Ilansen, L. B. L., Holm, A., and Dana, K (1998) *Photoaffinity Labeling of the Human Receptor for Urokinase-Type Plasminogen Activator Using a Decapeptide Antagonist, Evidence for a Composite Ligand-Binding Site and a Short Interdomain Separation, Biochemistry* 37, 3612–3622). However, this methodology has a limited application because once introduced into peptides, this specified site is no longer available for modification with other reporter molecules. Thus, improved methods for producing site-specific modified proteins are desired.

SUMMARY OF THE INVENTION

The present invention relates to site-specific modified proteins and methods for their production. The present invention also relates to methods for labeling the site-specific modified proteins and methods for using the labeled site-specific modified proteins in structural and functional analyses of proteins.

In one aspect of the invention, amino acid analogs with selective reactivity other than with the lysine or cysteine side chains (—$NH_2$ and —SH functional groups) and proteins incorporating such amino acid analogs are disclosed. Such amino acid analogs allow for the incorporation of labels into a protein without modification of cysteine and lysine residues involved in protein function (e.g., nucleic acid binding proteins requiring lysine side chains for nucleic acid recognition and cysteine side chains for metal coordination such as zinc finger structures). In a further aspect of the invention, methods for producing site-specific modified proteins, including proteins that incorporate amino acid analogs, are disclosed. In yet a further aspect of the invention, site-specific modified proteins are site-specifically labeled. A further aspect of the invention discloses methods for employing labeled site-specific modified proteins in structural and functional analysis of proteins.

In another aspect of the invention, methods for labeling proteins without modifying lysine and cysteine residues are disclosed. These methods involve preparation of site-specific modified proteins with amino acid analogs and subsequent labeling of the site-specific modified protein at the site of the amino acid analog.

Another aspect of the invention discloses methods for analyzing protein-RNA interactions under physiological conditions. In one aspect of the invention, fluorescence resonance energy transfer systems are employed to determine binding affinities of proteins.

BRIEF DESCRIPTION OF THE DRAWING

FIG. 2(A). Fluorescence spectra of Tat-Fl (red) and Tat-Fl with TAR RNA-Rh (blue). The concentrations of TAR RNA-Rh, TAT-Rh and Tat-Fl were 3 and 5 nM, respectively.

FIG. 2(B). Fluorescence intensity of Tat-Fl (5 nM) at 512 nm in the presence of increasing TAR-Rh concentrations. The solid line represents the best fits of the data by nonlinear regression to quadratic equation (1). The fluorescence measurements were performed on PTI fluorescence spectrophotometer controlled by Felix software. The excitation wavelength was 492 nm and slits width was set 3.5 nm for both excitation and emission. All samples were corrected for the light source excitation effect and for the background intensity of buffer fluorescence as well as for dilution factors. Buffer conditions: 50 nM Tris-HCl, pH 7.4 at 25° C., 20 mM KCl.

DETAILED DESCRIPTION OF THE INVENTION

Site specific modification of proteins and peptides provides a powerful research tool in chemistry and biology. The present invention relates to site-specific modified proteins and methods for making the same.

In one embodiment of the invention, site-specific modified proteins comprising an amino acid analog substituted at the desired site of modification are disclosed. The term "amino acid analog" refers to an amino acid with a modified side chain. The amino acid analogs of the present invention have selective reactivity, allow for further modification upon being incorporated into a protein, and do not affect the biological activity of the protein. The amino acid analogs of the present invention include, but are not limited to, analogs of tyrosine, including, Acetyl-Tyr and Formyl-Tyr. With respect to selective reactivity, the amino acid analogs are preferably non-reactive with lysine and cysteine residues. Selective reactivity refers to the amino acid analog's ability to react with certain amino acid residues while not reacting with others, preferably the amino acid analog is non-reactive with residues that affect the biological activity of the protein. The term "biological activity" refers to the ability of a protein to carry out its normal or specified functions, including, but not limited to, its ability to interact with and/or bind to proteins, nucleic acids and ligands. Amino acid analogs that alter protein structure or the character of the protein and thereby inhibit the normal function of the protein impair the biological activity of the protein. The term "protein" includes proteins, polypeptides and fragments of proteins or peptides which retain the desired biological activity of any protein of interest.

Another embodiment of the invention involves methods for producing site-specific modified proteins. The methods comprise the steps of synthesizing an amino acid analog to be incorporated at a desired site in the protein and incorporating the amino acid analog into the protein at the desired site, thereby producing a site-specific modified protein. A further embodiment involves site specifically labeling the site-specific modified protein. Labels include fluorescent dye molecules, fluorophores, such as fluorescein and fluorescein derivatives, and those containing reactive groups such as isothiocyanates, triazinates, and sulfonyl chlorides. The proteins and methods of this invention offer versatile procedures for labeling peptides of biological interest at a desired site and provide tools for post-synthetic peptide modification and the structural and functional analysis of proteins through the introduction of biophysical probes. They also allow for the labeling of proteins where several nucleophilic side chains of lysine and cysteine are present.

In another embodiment, methods for labeling proteins, without modifying lysine and cysteine side chains, are disclosed. In this embodiment, an amino acid of the protein at the desired location of labeling is replaced with an amino acid analog to produce a site-specific modified protein. The site-specific modified protein is then labeled at the location of the amino acid analog of the protein.

One skilled in the art will recognize that the site-specific modified proteins and methods of the invention may be employed to probe protein-RNA interactions as well as protein-protein interactions. RNA molecules can fold into extensive structures containing regions of double-stranded duplex, hairpins, internal loops, bulged bases and pseudoknotted structures. (Tinoco, I., Jr., Puglisi, J. D., and Wyatt, J. R. (1990) *RNA folding, Nucl. Acids & Mol. Biol.* 4, 205–226). The three-dimensional structures of RNA create binding sites for specific interactions with proteins. One example of such interactions is the mechanism of transactivation of human immunodeficiency virus type 1 (HIV-1) gene expression that requires the interaction of Tat protein with the trans-activation responsive region (TAR) RNA, a 59-base stem-loop structure located at the 5'-end of all nascent HIV-1 transcripts. (Berkhout, B., Silverman, R. II, and Jeang, K. T. (1989) *Tat trans-activates the Human Immunodeficiency Virus Through a Nascent RNA Target, Cell* 59, 273–82; Jones, K. A., and Peterlin, B. M. (1994) *Control of RNA Initiation and Elongation at the HIV-1 Promoter, Annu. Rev. Biochem.* 63, 717–43; Jones, K. A. (1997) *Taking a New TAK on Tat Transactivation, Genes & Dev.* 11, 2593–2599; Cullen, B. R. (1998) *HIV-1 auxiliary proteins: making connections in a dying cell, Cell* 93, 685–692). TAR RNA contains a six-nucleotide loop and a three-nucleotide pyrimidine bulge which separates two helical stem regions (FIG. 1(A)). (Berkhout, B., Silverman, R. II, and Jeang, K. T. (1989) *Tat trans-activates the Human Immunodeficiency Virus Through a Nascent RNA Target, Cell* 59, 273–82; Rosen, C. A., Sodroski, J. G., and Haseltine, W. A. (1985) *Location of Cis-acting Regulatory Sequences in the Human T cell Lymphotropic Virus type III (HTLV-III/LAV) Long Terminal Repeat, Cell* 41, 813–823; Muesing, M. A., Smith, D. H., and Capon, D. A. (1987) *Regulation of mRNA by a Human Immunodeficiency Virus trans-activator protein, Cell* 48, 691–701; Jakobovits, A., Smith, D. H., Jakobovits, E. B., and Capon, D. J. (1988) *A discrete Element* 3 *of Human Immunodeficiency Virus* 1 *(HIV-*1) *and HIV-*2 *mRNA Initiation Sites Mediates Transcriptional Activation by an HIV Trans Activator, Mol. Cell. Biol.* 8, 2555–2561). The trinucleotide bulge is essential for high affinity and specific binding of the Tat protein. (Dingwall, C. Ernberg, I., Gait, M. J., Green, S. M., Heaphy, S., Karn, J., Lowe, A. D., Singh, M., Skinner, M. A., and Valerio, R. (1989) *Human Immunodeficiency Virus Tat protein Binds Trans-activation-responsive Region (TAR) RNA in vitro. Proc. Natl. Acad. Sci.* 86, 6925–6929; Dingwall, C., Ernberg, J., Gait, M. J., Green, S. M., Heaphy, S., Karn, J., Lowe, A. D., Singh, M., and Skinner, M. A. (1990) *HIV-*1 *Tat Protein Stimulations Transcription by Binding to the Stem of the TAR RNA Structure. EMBO J.* 9, 4145–4153). Tat protein binds TAR RNA in vitro with high affinity. Due to difficulties in Tat purification, small Tat peptides that specifically bind TAR RNA with high affinity have been used in many Tat-TAR studies. (Weeks, K. M., and Crothers, D. M. (1991) *RNA Recognition by Tat-Derived Peptides: Interaction in the Major Groove? Cell* 66, 577–588; Calman, B. J., Tidor, B., Biancalana, S., Hudson, D., and Frankel A. D.

(1991) *Arginine-Mediated RNA Recognition: The Arginine Fork, Science* 252, 1167–1171; Calnan, B. J., Biancalana, S., Hudson, D., and Frankel, A. D. (1991) *Analysis of Arginine-Rich Peptides from the HIV Tat Protein Reveals Unusual Features of RNA Protein Recognition, Genes Dev.* 5, 201–210; Churcher, M. J., Lamont, C., Hamy, F., Dingwall, C., Green, S. M., Lowe, A. D., Butler, P. J. C., Gait, M. J., and Karn, J. (1993) *High Affinity Binding of TAR RNA by the Human Immunodeficiency Virus Type-1 tat Protein Requires Base-pairs in the RNA Stem and Amino Acid Residues Flanking the Base Region, J. Mol. Biol.* 230, 90–110; Long, K. S., and Crothers, D. M. (1995) *Interaction of human immunodeficiency virus type 1 Tat-derived peptides with TAR RNA, Biochemistry* 34, 8885–8895; Wang, Z., and Rana, T. M. (1996) *RNA conformation in the Tat-TAR complex determined by site-specific photo-cross-linking, Biochemistry* 35, 6491–6499; Huq, I., and Rana T. M. (1997) *Probing the proximity of the core domain of an HIV-1 Tat fragment in a Tat-TAR complex by affinity cleaving, Biochemistry* 36, 12592–12599). Since Tat-derived peptides which contain the basic arginine-rich region of Tat are able to form in vitro complexes with TAR RNA (Weeks, K. M., and Crothers, D. M. (1991) *RNA Recognition by Tat-Derived Peptides: Interaction in the Major Groove? Cell* 66, 577–588; Calnan, B. J., Biancalana, S., Hudson, D., and Frankel, A. D. (1991) *Analysis of Arginine-Rich Peptides from the HIV Tat Protein Reveals Unusual Features of RNA Protein Recognition, Genes Dev.* 5, 201–210; Churcher, M. J., Lamont, C., Hamy, F., Dingwall, C., Green, S. M., Lowe, A. D., Butler, P. J. C., Gait, M. J., and Karn, J. (1993) *High Affinity Binding of TAR RNA by the Human Immunodeficiency Virus Type-1 tat Protein Requires Base-pairs in the RNA Stem and Amino Acid Residues Flanking the Base Region, J. Mol. Biol.* 230, 90–110), these peptides provide a well-characterized system to test new probes to study RNA-protein interactions. Although Tat peptides-TAR-binding affinities have been well studied by electrophoretic mobility shift assays, there is no available data reporting Tat peptide-TAR affinities in solution under physiological conditions.

Figure 3:
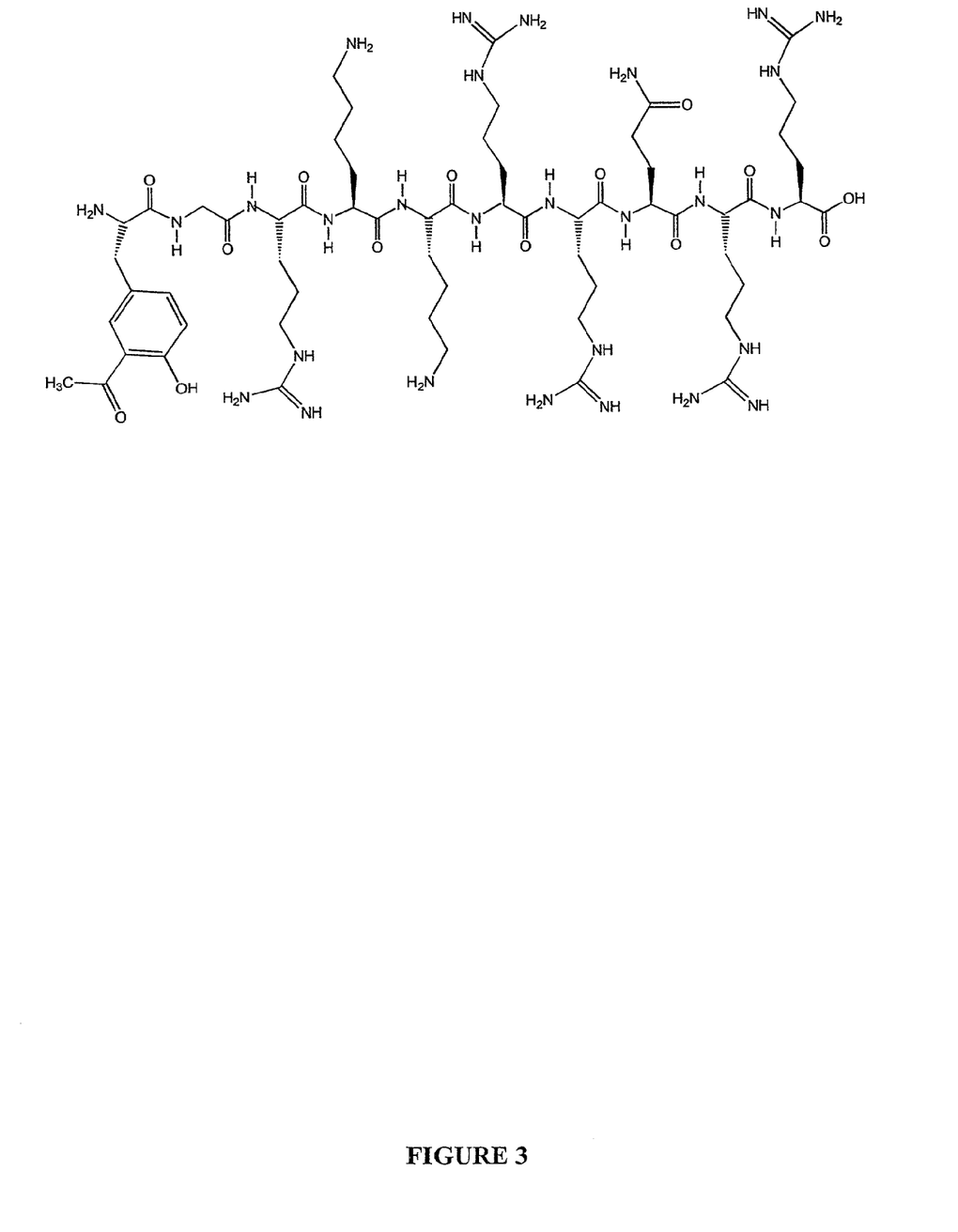
FIG. 3. Structure of the Tat (amino acids 47 to 56) peptide containing 3-acetyl-tyrosine.
Figure 4:
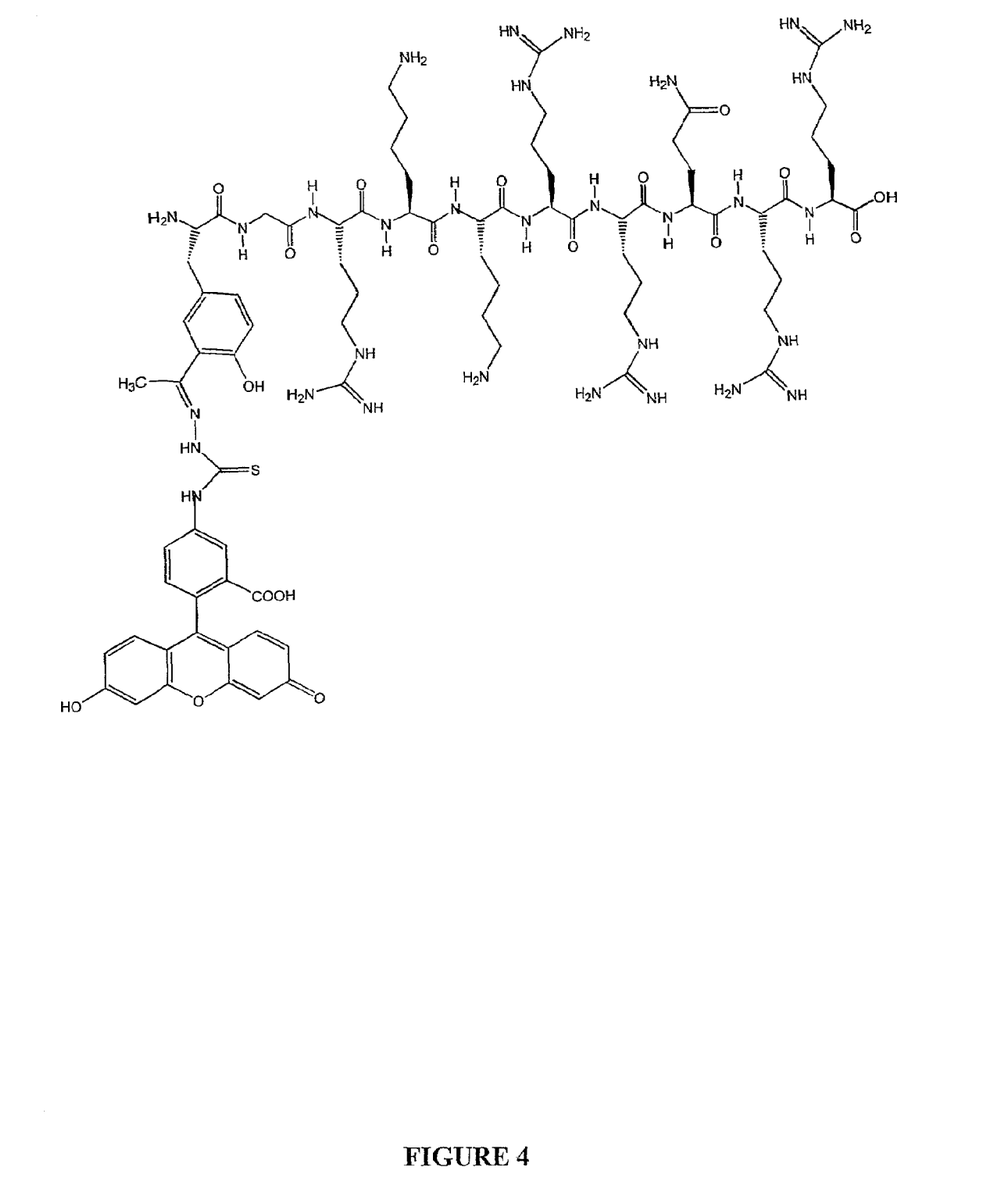
FIG. 4. Structure of the Tat (amino acids 47 to 56) peptide containing 3-acetyl-tyrosine conjugated with fluorescein.
Figure 7:
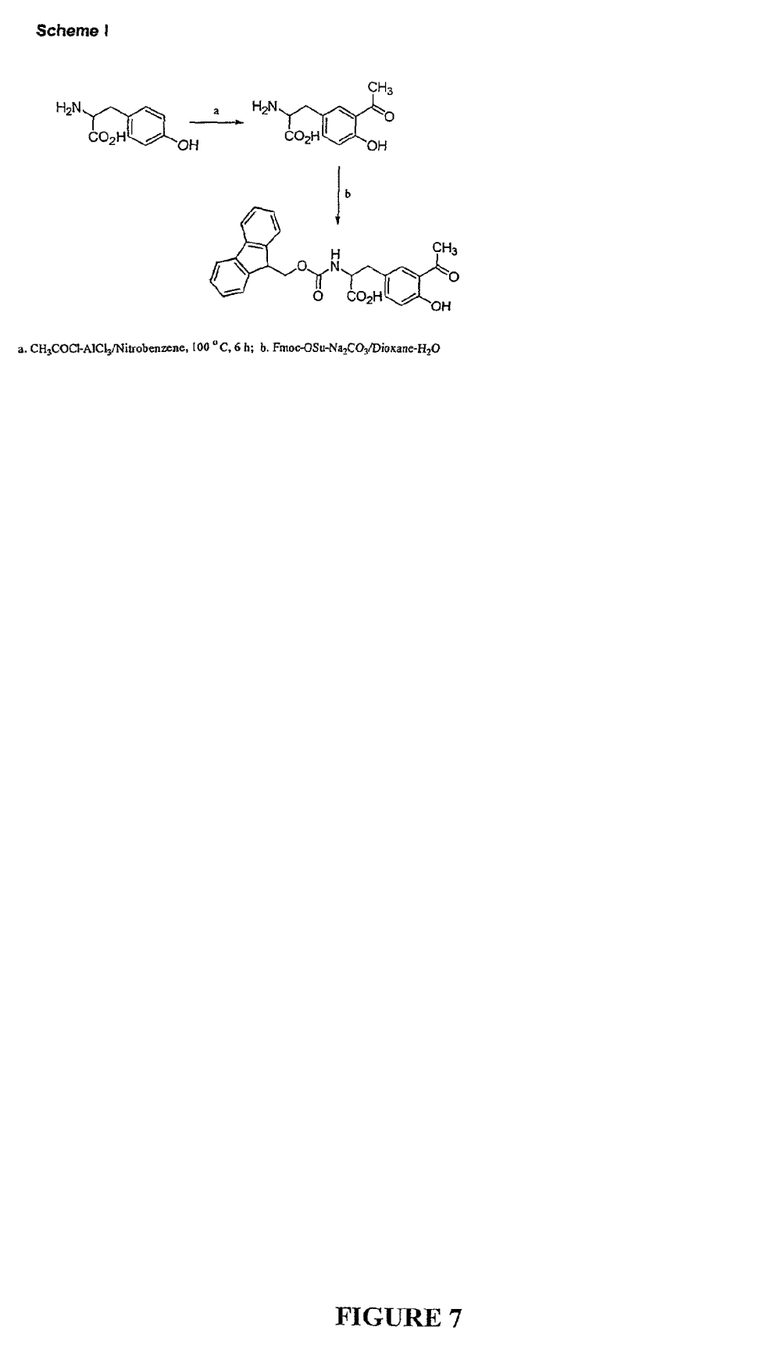
FIG. 7. Scheme I—(a) Synthesis of 3-Acetyl-tyrosine from tyrosine by Friedel-Crafts reaction, (b) Conversion of 3-Acetyl-tyrosine to its Fmoc derivative by Fmoc-Osu reaction.

As a model system, a Tyrosine analog, 3-Acetyl-Tyrosine, was synthesized for use in the selective modification of proteins. The side chain of tyrosine has been modified with a keto functional group without disrupting its potential phosphorylation and metal coordination site (Ranganathan, S., and Tamilarasu, N. (1999) *Protein Engineering: Design of Single-Residue Anchored Metal-Uptake Systems, Inorg. Chem.* 38, 1019–1023), and its Fmoc derivative has been used in standard solid phase peptide synthesis (FIG. 7, Scheme I). The human immunodeficiency virus type 1 (HIV-1) Tat peptide (amino acids 47–56) containing the arginine rich RNA-binding region was synthesized. The Tyr-47 of the Tat peptide was replaced with 3-Acetyl-Tyrosine resulting in a site-specific modified protein, Acetyl-Tyr-Tat peptide. (FIG. 1(B), FIG. 3, FIG. 7). The Acetyl-Tyr-Tat peptide was subsequently labeled with a fluorescein derivative (FIG. 4, FIG. 8—Scheme II) to study RNA-protein interactions. Fluorescence energy transfer experiments were conducted. Results of the fluorescence energy transfer experiments showed that the Acetyl-Tyr-Tat peptide binds to the rhodamine labeled TAR RNA with a dissociation constant ($K_D$) of 1.0±0.5 nM.

In another embodiment of the invention, methods for analyzing protein-RNA interactions under physiological conditions are disclosed. In one aspect, the protein is a site-specific modified protein labeled with a donor dye molecule and the RNA is labeled with an acceptor dye molecule. The donor dye molecule must be a fluorophore, while the acceptor dye molecule is usually a fluorophore, although it does not have to be. The donor molecule transfers energy to the acceptor molecule. This energy transfer, which is measured, occurs over distances in the 10–70 Å range. The emission of each the protein mixture and the RNA mixture is measured respectively. Then, the RNA mixture is added to the protein mixture and the emission of the mixture is measured. The interaction between the protein and RNA is calculated through comparison of the emission measurements for each mixture. In another aspect, protein-protein interactions may be analyzed wherein a donor labeled site-specific modified protein and acceptor labeled protein are employed. A donor labeled site-specific modified protein and an acceptor labeled site-specific modified protein may also be used in this method.

EXAMPLE 1

Synthesis 3-Acetyl-Tyrosine and
3-Acetyl-Tyrosine-Tat Peptide

Figure 5:
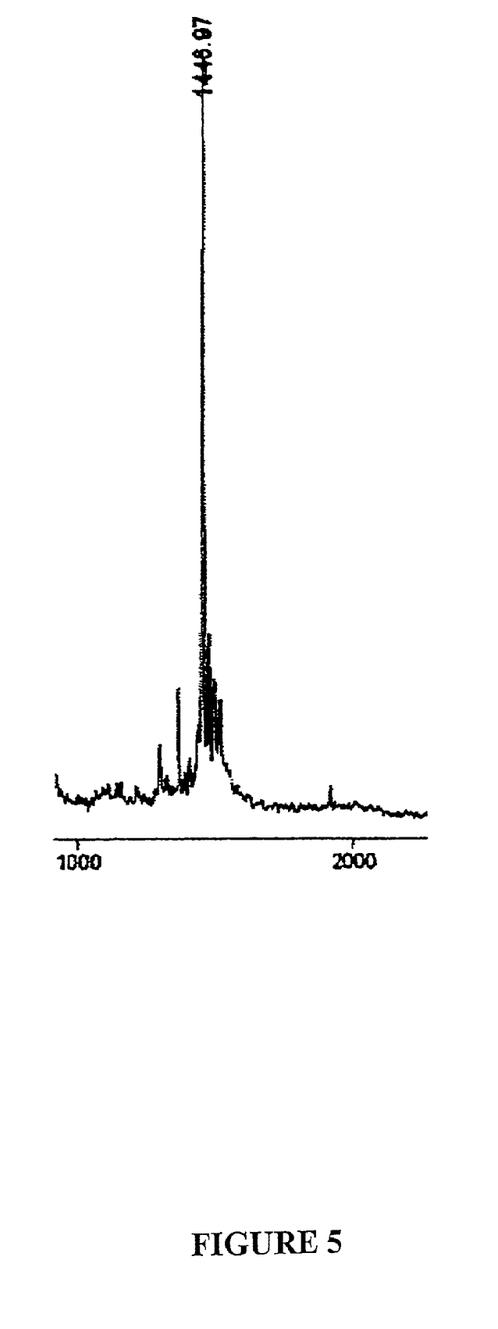
FIG. 5. MALDI/TOF mass spectrum of the Tat (amino acids 47 to 56) peptide containing 3-acetyl-tyrosine. Calculated mass for [M+H]$^+$—1446.6, found 1446.97.

3-Acetyl-tyrosine was synthesized from tyrosine by Friedel-Crafts reaction and converted to its Fmoc derivative by Fmoc-Osu reaction (FIG. 7, Scheme I). Tat-derived peptide (from amino acids 47–56) was synthesized on an Applied Biosystems 431A peptide synthesizer using standard FastMoc protocols. Cleavage and deprotection of the peptide was carried out in 2 mL Reagent K for 6 h at rt. Reagent K contained 1.75 ml, TFA, 100 µl water, and 50 µL of ethanodithiol. (King, D. S., Fields, C. G., and Fields, G. B. (1990) *A cleavage method which minimizes side reactions following Fmoc solid phase peptide synthesis, Int J. Peptide Protein Res.* 36, 255–266). After cleavage from the resin, peptide was purified by HPLC on a Zorbax 3000 SB-$C_8$ column. The mass of fully deprotected and purified peptide was confirmed by MALDI mass spectrometry (FIG. 5). The presence of this 3-acetyl-tyrosine in a peptide can easily be detected by monitoring the absorption spectrum because 3-acetyl-tyrosine gives a unique UV spectrum with absorption maxima at 254 nm (5915 $cm^{-1}M^{-1}$) and 330 nm (1643 $cm^{-1}M^{-1}$).

EXAMPLE 2

Site-Specific Labeling of the 3-Acetyl-Tyr in the
Protein

Figure 6:
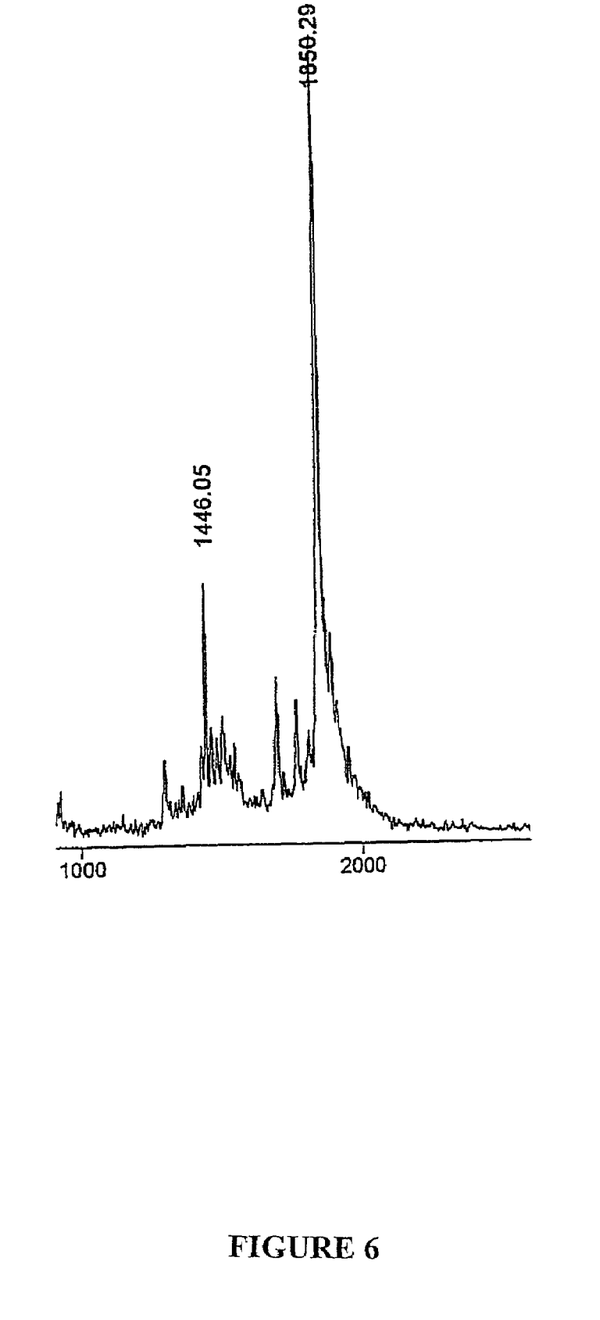
FIG. 6. MALDI/TOF mass spectrum of the Tat (amino acids 47 to 56) peptide containing 3-acetyl-tyrosine conjugated with fluorescein. Calculated mass for [M+H]$^+$—1849.7 found 1850.29.
Figure 8:
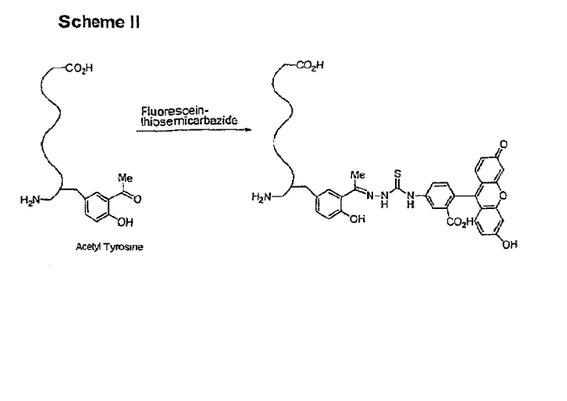
FIG. 8. Scheme II—Site-specific labeling of Acetyl-Tyr-Tat peptide with a dye.

To site-specifically label the acetyl-Tyr containing Tat peptide with a dye, we used a semicarbazide derivative of fluorescein that modified acetyl-Tyr side chain through a semicarbazone linkage (FIG. 8, Scheme II). This reaction was carried out by the addition of 2 equivalents of 30 mM solution of fluorescein-5-thiosemicarbazide in DMF to 1 mM solution of the peptide in conjugation buffer (10 mM potassium phosphate pH 7.0, 50% DMF), and incubating the reaction mixture at 4° C. overnight. The peptide-fluorescein conjugate was purified by reverse phase HPLC and characterized by MALDI/TOF mass spectrometry (FIG. 6). The conjugation reaction of the dye to acetyl-Tyr peptide was very efficient and resulted in ~80% yields. Although this Tat peptide contains two lysine residues in its sequence, these $NH_2$ groups do not react with acetyl-tyrosine to form the imine linkage because the reaction is highly reversible under the conjugation conditions.

EXAMPLE 3

Synthesis of TAR RNA

The secondary structure of TAR RNA used in this invention is provided at FIG. 1(A). TAR RNA spans the minimal sequences that are required for Tat responsiveness in vivo, (Jakobovits, A., Smith, D. H., Jakobovits, E. B., and Capon, D. J. (1988) *A discrete Element 3 of Human Immunodeficiency Virus 1 (HIV-1) and HIV-2 mRNA Initiation Sites Mediates Transcriptional Activation by an HIV Trans Activator, Mol. Cell. Biol.* 8, 2555–2561) and for in vitro binding of Tat-derived peptides (Cordingley, M. G., La Femina, R. L., Callahan, P. L., Condra, J. H., Sardana, V. V., Graham, D. J., Nguyen, T. M., Le Grow, K., Gotlib, L., Schlabach, A. J., and Colonno, R. J. (1990) *Sequence specific Interaction of Tat protein and Tat peptides with the Transactivation-responsive Sequence Element of Human Immunodeficiency Virus Type 1 in vitro, Proc. Natl. Acad. Sci.* 87, 8985–8989). Chemical syntheses were performed on ABI synthesizer Model 392 using standard protocols. All the monomers of (2 cyanoethyl) phosphoramidites were obtained from Glen Research (Sterling, Va.). TAR RNA was chemically synthesized on a rhodamine-containing CPG 500 support. Synthesis of RNA, deprotection, characterization, and purification were performed as described earlier. (Shah, K., Wu, H., and Rana, T. M. (1994) *Synthesis of uridine phosphoramidite analogs: Reagents for site-specific incorporation of photoreactive sites into RNA sequences, Bioconjugate Chem.* 5, 508–512; Ping, Y. -H., Liu, Y., Wang, X., Neenhold, H. R., and Rana, T. M. (1997) *Dynamics of RNA-protein interactions in the HIV-1 Rev-RRE complex visualized by 6-thioguanosine-mediated photocrosslinking, RNA* 3, 850–860).

EXAMPLE 4

FRET System—Analysis of Protein-RNA Interaction

Figure 1:
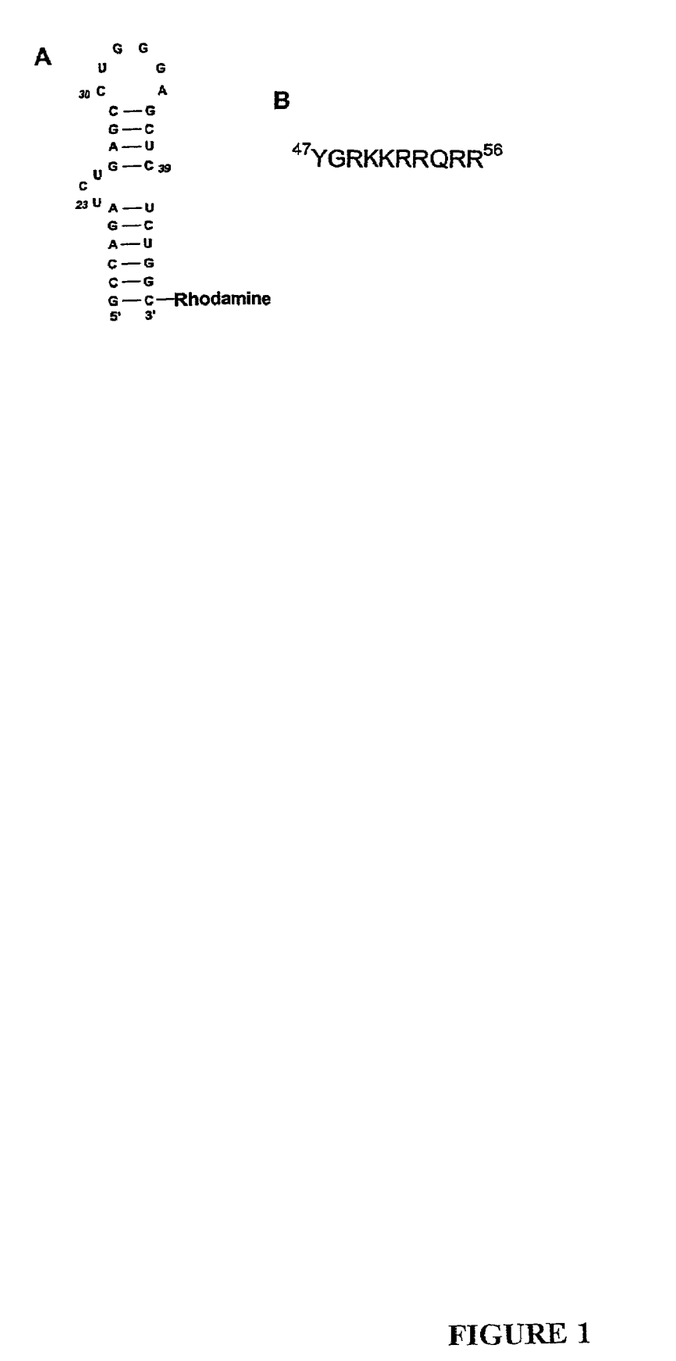
FIG. 1(A). Secondary structure of TAR RNA used in this invention (SEQ ID NO: 1).
FIG. 1(B). The Tat-derived peptide, amino acids 47 to 56 (SEQ ID NO: 2), contains the RNA-binding region of Tat protein. The Acetyl-Tyr is incorporated at position 47 (SEQ ID NO: 3) and modified with fluorescein (see FIG. 8).

To determine the binding affinities of a Tat peptide under physiological conditions and test the application of acetyl-Tyr, we developed a fluorescence resonance energy transfer (FRET) system containing TAR RNA and a Tat peptide uniquely labeled with donor and acceptor dye molecules (FIG. 1). FRET, in which a fluorescent donor molecule transfer energy via a non-radiative dipole-dipole interaction to an acceptor molecule (which is usually also a fluorescent molecule) is a standard spectroscopic technique for measuring distances in the 10–70 Å range. (Clegg, R. M. (1992) *Fluorescence resonance energy transfer and nucleic acids, Methods Enzymol.* 211, 353–88; Yang, M., and Millar, D. P. (1997) *Fluorescence resonance energy transfer as a probe of DNA structure and function, Methods Enzymol.* 278, 417–444). The donor's lifetime and quantum yield are reduced upon energy transfer, and the acceptor fluorescence is increased, or sensitized. Quantification of the efficiency of energy transfer allows determination of the distance between the two fluorophores. We used a well-characterized donor acceptor dye-pair, fluorescein-rhodamine, for FRET experiments.

Figure 2:
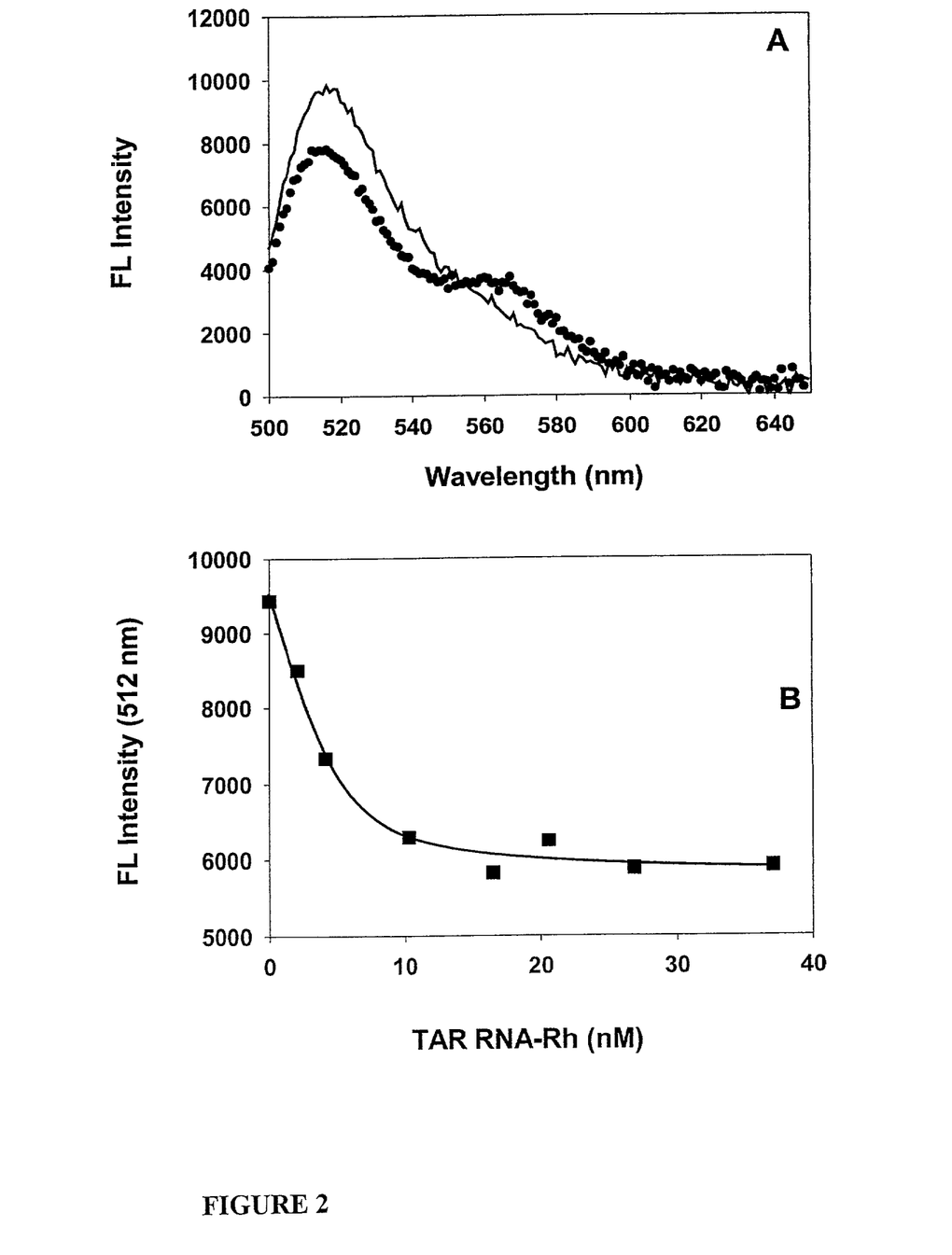

We examined FRET between the fluorescein labeled Tat peptide (Tat-Fl) and rhodamine labeled TAR RNA (TAR-Rh) (FIG. 1). Emission scans from 500 to 650 nm of Tat-Fl (red) and Tat-Fl with TAR-Rh (blue) were recorded (FIG. 2(A)). Tat-Fl has an emission maximum around 512 nm (red), whereas upon adding TAR RNA-Rh (blue), this peak is decreased and another peak at 575 nm is increased. This reduction in fluorescein emission and the corresponding increase in rhodamine emissions were due to the resonance energy transfer from Tat-Fl to TAR-Rh. To determine the binding affinity between the Tat peptide and TAR RNA, we examined fluorescence quenching of Tat-Fl at several different TAR-Rh concentrations (FIG. 2(B)). The solid line in FIG. 2(B) represents the best fits of the data by nonlinear regression to quadratic equation (1). The fluorescence measurements were performed on PTI fluorescence spectrophotometer controlled by Felix software. The excitation wavelength was 492 nm and slits width was set 3.5 nm for both excitation and emission. All samples were corrected for the light source excitation effect and for the background intensity of buffer fluorescence as well as for dilution factors. Buffer conditions: 50 mM Tris-HCl, pH 7.4 at 25° C., 20 mM KCl. $K_D$ values were calculated by fitting data to quadratic equation (1).

$$F - F_{min} = \{(F_{max} F_{min})[(R + P_0 + K) - ((R + P_0 + K)^2 - 4RP_0)^{1/2}]\}/2P_0 \quad (1)$$

Where F is the relative fluorescent intensity, $F_{min}$ is the fluorescent intensity at the start of the titration, $F_{max}$ is the fluorescent intensity at saturating concentration of RNA, R, $P_0$ is the total concentration of Tat-Fl. K is the dissociation constant of the RNA and Tat peptide and can be obtained by fitting data to equation (1). (Muller, B., Restle, T., Reinstein, J., and Goody, R. S. (1991) *Interaction of fluorescently labeled dideoxynucleotides with HIV-1 reverse transcriptase, Biochemistry* 30, 3709–3715). Our results showed that Tat-Fl binds to the TAR Rh with a dissociation constant ($K_D$) of 1.0±0.5 nM.

The selective protein modification methods of this invention offer versatile procedures for labeling proteins of biological interest at a desired site, even in the presence of several nucleophilic side chains of lysine and cysteine. These methods provide tools for post-synthetic peptide modification and for structural and functional analysis of proteins through the introduction of biophysical probes.

One skilled in the art will readily appreciate that the present invention is well adapted to carry out the objects and obtain the ends and advantages mentioned as well as those inherent therein. The amino acid analogs along with the methods and procedures described herein are presently representative of preferred embodiments and are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein within departing from the scope and spirit of the invention.

All patents and publications referenced herein are incorporated by reference to the same extent as if each individual publication was specifically and individually indicated to be

REFERENCES

1. Means, G. E., and Feeney, R. E. (1990) Chemical modification of proteins: history and application, *Bioconjugate Chem.* 1, 2–12.
2. Geoghegan, K. F., and Stroh, J. G. (1992) Site-Directed Conjugation of Nonpeptide Groups to Peptides and Proteins via Periodate Oxidation of a 2-Amino Alcohol, Application to Modification at N-Terminal Serine, *Bioconjugate Chem.* 3, 138–146.
3. Cornish, V. W., Hahn, K. M., and Schultz, P. G. (1996) Site-Specific Protein Modification Using a Ketone Handle, *J. Am. Chem. Soc.* 118, 8150–8151.
4. Falchetto, R., Vorherr, T., Brunner, J., and Carafoli, E. (1991) The Plasma Membrane Ca 2+ Pump Contains a Site That Interacts with Its Calmodulin-binding Domain, *J. Biol. Chem.* 266, 2930–2936.
5. Lohse, J., Neilson, P. E., Ilarrit, N., and Dahl, O. (1997) Fluorescein-Conjugated Lysine Monomers for Solid Phase Synthesis of Fluorescent Peptides and PNA Oligomers, *Bioconjugate Chem.* 8, 503–509.
6. Dong, C. Z., De Roequigny, H., Remy, E., Mellac, S., Fournic-Zaluski, M. C., and P., R. B. (1997) Synthesis and biological activities of fluorescent acridine-containing HIV-1 proteins for investigation of nucleic acid-$NC_p7$ interactions. *J. Peptide Res.* 50, 269–278.
7. Ploug, M., Ostergaard, S., Ilansen, L. B. L., Holm, A., and Dana, K. (1998) Photoaffinity Labeling of the Human Receptor for Urokinase-Type Plasminogen Activator Using a Decapeptide Antagonist, Evidence for a Composite Ligand-Binding Site and a Short Interdomain Separation, *Biochemistry* 37, 3612–3622.
8. Ranganathan, S., and Tamilarasu, N. (1999) Protein Engineering: Design of Single-Residue Anchored Metal-Uptake Systems, *Inorg. Chem.* 38, 1019–1023.
9. King, D. S., Fields, C. G., and Fields, G. B. (1990) A cleavage method which minimizes side reactions following Fmoc solid phase peptide synthesis, *Int J. Peptide Protein Res.* 36, 255–266.
10. See Supporting Information.
11. Tinoco, I., Jr., Puglisi, J. D., and Wyatt, J. R. (1990) RNA folding, *Nucl. Acids & Mol. Biol.* 4, 205–226.
12. Berkhout, B., Silverman, R. II, and Jeang, K. T. (1989) Tat trans-activates the Human Immunodeficiency Virus Through a Nascent RNA Target, *Cell* 59, 273–82.
13. Jones, K. A., and Peterlin, B. M. (1994) Control of RNA Initiation and Elongation at the HIV-1 Promoter, *Annu. Rev. Biochem.* 63, 717–43.
14. Jones, K. A. (1997) Taking a New TAK on Tat Trans-activation, *Genes & Dev.* 11, 2593–2599.
15. Cullen, B. R. (1998) HIV-1 auxiliary proteins: making connections in a dying cell, *Cell* 93, 685–692.
16. Rosen, C. A., Sodroski, J. G., and Haseltine, W. A. (1985) Location of Cis-acting Regulatory Sequences in the Human T cell Lymphotropic Virus type III (HTLV-III/LAV) Long Terminal Repeat, *Cell* 41, 813–823.
17. Muesing, M. A., Smith, D. H., and Capon, D. A. (1987) Regulation of mRNA by a Human Immunodeficiency Virus trans-activator protein, *Cell* 48, 691–701.
18. Jakobovits, A., Smith, D. H., Jakobovits, E. B., and Capon, D. J. (1988) A discrete Element 3 of Human Immunodeficiency Virus 1 (HIV-1) and HIV-2 mRNA Initiation Sites Mediates Transcriptional Activation by an HIV Trans Activator, *Mol. Cell. Biol.* 8, 2555–2561.
19. Dingwall, C. Ernberg, I., Gait, M. J., Green, S. M., Heaphy, S., Karn, J., Lowe, A. D., Singh, M., Skinner, M. A., and Valerio, R. (1989) Human Immunodeficiency Virus Tat protein Binds Trans-activation-responsive Region (TAR) RNA in vitro. *Proc. Natl. Acad. Sci.* 86, 6925–6929.
20. Dingwall, C., Ernberg, J., Gait, M. J., Green, S. M., Heaphy, S., Karn, J., Lowe, A. D., Singh, M., and Skinner, M. A. (1990) HIV-1 Tat Protein Stimulations Transcription by Binding to the Stem of the TAR RNA Structure. *EMBO J.* 9, 4145–4153.
21. Weeks, K. M., and Crothers, D. M. (1991) RNA Recognition by Tat-Derived Peptides: Interaction in the Major Groove? *Cell* 66, 577–588.
22. Calman, B. J., Tidor, B., Biancalana, S., Hudson, D., and Frankel A. D. (1991) Arginine-Mediated RNA Recognition: The Arginine Fork, *Science* 252, 1167–1171.
23. Calnan, B. J., Biancalana, S., Hudson, D., and Frankel, A. D. (1991) Analysis of Arginine-Rich Peptides from the HIV Tat Protein Reveals Unusual Features of RNA Protein Recognition, *Genes Dev.* 5, 201–210.
24. Churcher, M. J., Lamont, C., Hamy, F., Dingwall, C., Green, S. M., Lowe, A. D., Butler, P. J. C., Gait, M. J., and Karn, J. (1993) High Affinity Binding of TAR RNA by the Human Immunodeficiency Virus Type-1 tat Protein Requires Base-pairs in the RNA Stem and Amino Acid Residues Flanking the Base Region, *J. Mol. Biol.* 230, 90–110.
25. Long, K. S., and Crothers, D. M. (1995) Interaction of human immunodeficiency virus type 1 Tat-derived peptides with TAR RNA, *Biochemistry* 34, 8885–8895.
26. Wang, Z., and Rana, T. M. (1996) RNA conformation in the Tat-TAR complex determined by site-specific photo-cross-linking, *Biochemistry* 35, 6491–6499.
27. Huq, I., and Rana T. M. (1997) Probing the proximity of the core domain of an HIV-1 Tat fragment in a Tat-TAR complex by affinity cleaving, *Biochemistry* 36, 12592–12599.
28. Clegg, R. M. (1992) Fluorescence resonance energy transfer and nucleic acids, *Methods Enzymol.* 211, 353–88.
29. Yang, M., and Millar, D. P. (1997) Fluorescence resonance energy transfer as a probe of DNA structure and function, *Methods Enzymol.* 278, 417–444.
30. Muller, B., Restle, T., Reinstein, J., and Goody, R. S. (1991) Interaction of fluorescently labeled dideoxynucleotides with HIV-1 reverse transcriptase, *Biochemistry* 30, 3709–3715.
31. Cordingley, M. G., La Femina, R. L., Callahan, P. L., Condra, J. H., Sardana, V. V., Graham, D. J., Nguyen, T. M., Le Grow, K., Gotlib, L., Schlabach, A. J., and Colonno, R. J. (1990) Sequence specific Interaction of Tat protein and Tat peptides with the Transactivation-responsive Sequence Element of Human Immunodeficiency Virus Type 1 in vitro, *Proc. Natl. Acad. Sci.* 87, 8985–8989.
32. Shah, K., Wu, H., and Rana, T. M. (1994) Synthesis of uridine phosphoramidite analogs: Reagents for site-specific incorporation of photoreactive sites into RNA sequences, *Bioconjugate Chem.* 5, 508–512.
33. Ping, Y. -H., Liu, Y., Wang, X., Neenhold, H. R., and Rana, T. M. (1997) Dynamics of RNA-protein interactions in the HIV-1 Rev-RRE complex visualized by 6-thioguanosine-mediated photocrosslinking, *RNA* 3, 850–860.

What is claimed is:

1. A method for determining protein-RNA interactions under simulated physiological conditions, the method comprising:
   (a) synthesizing a site specific modified protein, wherein the site specific modified protein comprises a protein modified by replacement of an amino acid, other than lysine or cysteine residues, with an analog of the amino acid, wherein the amino acid analog does not affect a biological activity of the protein;
   (b) subsequently site-specifically labeling the site specific modified protein at the site of the amino acid analog with a donor dye molecule, wherein the site-specific labeling is capable of occurring in the absence of orthogonal protection of nucleophilic side chains of lysine and cysteine;
   (c) providing a RNA molecule labeled with an acceptor dye molecule, wherein the acceptor dye molecule is capable of participating in fluorescence resonance energy transfer with the donor dye molecule;
   (d) measuring the emission of the labeled protein and labeled RNA in (b) and (c) respectively;
   (e) combining the labeled RNA in (c) with the labeled protein in (b) to form a mixture;
   (f) measuring the emission of the mixture in (e); and,
   (g) determining the proximity between the donor dye molecule and the acceptor dye molecule.

2. The method of claim 1, wherein the dye pair is fluorescein-rhodamine.

3. The method of claim 1, wherein the site-specific modified protein is an Acetyl-Tyr-Tat peptide having the following sequence: Xaa Gly Mg Lys Lys Mg Arg Gin Mg Mg (SEQ ID NO:3), wherein Xaa is Acetyl-Tyr, which is represented by the following structure:

4. The method of claim 3, wherein the RNA is TAR RNA.

5. The method of claim 1, further comprising comparing the emission measurements from (d) and (f) to determine if fluorescence resonance energy transfer has occurred.

6. The method of claim 1, wherein the replaced amino acid is Tyrosine.

7. The method of claim 6, wherein the amino acid analog has the following structure:

8. The method of claim 1, wherein the protein is a Tat peptide represented by SEQ ID NO:2.

9. The method of claim 1, wherein step (b) comprises conjugating the donor dye molecule to a functional group on the amino acid analog, which is selected from the group consisting of an acetyl group and a formyl group.

10. The method of claim 1, further comprising examining fluorescence quenching of the labeled protein at different concentrations of labeled RNA.

11. The method of claim 10, further comprising determining the binding affinity between the protein and the RNA.

* * * * *